(12) United States Patent
Wang et al.

(10) Patent No.: US 10,184,873 B2
(45) Date of Patent: Jan. 22, 2019

(54) VIBRATING WIRE VISCOMETER AND CARTRIDGE FOR THE SAME

(71) Applicant: Schlumberger Technology Corporation, Sugar Land, TX (US)

(72) Inventors: Cong Wang, Sagamihara (JP); Akira Kamiya, Sagamihara (JP); Yoko Morikami, Sagamihara (JP)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 146 days.

(21) Appl. No.: 14/850,915

(22) Filed: Sep. 10, 2015

(65) Prior Publication Data

US 2016/0090837 A1    Mar. 31, 2016

Related U.S. Application Data

(60) Provisional application No. 62/057,238, filed on Sep. 30, 2014.

(51) Int. Cl.
*G01N 11/16* (2006.01)
*G01N 33/28* (2006.01)

(52) U.S. Cl.
CPC ......... *G01N 11/16* (2013.01); *G01N 33/2823* (2013.01)

(58) Field of Classification Search
CPC ........ G01N 11/16; G01N 33/26; G01N 33/28; G01N 33/2823; G01L 1/106; E21B 47/011
USPC ............... 73/54.23–54.27, 54.41, 32 A, 431; 166/252.5
See application file for complete search history.

(56) References Cited

U.S. PATENT DOCUMENTS

| | | |
|---|---|---|
| 5,113,953 A | 5/1992 | Noble |
| 5,265,682 A | 11/1993 | Russell et al. |
| 5,503,385 A | 4/1996 | Tsushima et al. |
| 5,520,255 A | 5/1996 | Barr et al. |
| 5,553,678 A | 9/1996 | Barr et al. |
| 5,553,679 A | 9/1996 | Thorp |
| 5,582,259 A | 12/1996 | Barr |
| 5,603,385 A | 2/1997 | Colebrook |
| 5,673,763 A | 10/1997 | Thorp |

(Continued)

OTHER PUBLICATIONS

Goodwin et al, Vibrating Wire Viscometer with Wire Diameters of (0.05 and 0.15) mm: Results for Methylbenzene and Two Fluids with Nominal Viscosities at T) 298 K and p) 0.01 MPa of (14 and 232) mPaás at Temperatures between (298 and 373) K and Pressures below 40 MPa, 2005, J. Chem. Eng. Data 2005, 50, 647-655.*

(Continued)

*Primary Examiner* — Daniel S Larkin
*Assistant Examiner* — David L Singer
(74) *Attorney, Agent, or Firm* — Eileen Pape

(57) ABSTRACT

A vibrating wire viscometer and cartridge for the same are provided. The cartridge includes a body member with a flowline for passing fluid, an electrically conductive wire disposed in the flowline, first and second electrically conductive posts, and a connector having first and second electrically conductive terminals. The first and second posts are mechanically coupled to the body member to hold the wire in tension within the flowline. The first and second terminals are connected to the first and second posts for applying an alternating electric current to the wire, respectively.

6 Claims, 7 Drawing Sheets

(56) References Cited

U.S. PATENT DOCUMENTS

| | | | |
|---|---|---|---|
| 5,685,379 A | 11/1997 | Barr et al. | |
| 5,695,015 A | 12/1997 | Barr et al. | |
| 5,706,905 A | 1/1998 | Barr | |
| 5,778,992 A | 7/1998 | Fuller | |
| 5,803,185 A | 9/1998 | Barr et al. | |
| 5,971,085 A | 10/1999 | Colebrook | |
| 6,089,332 A | 7/2000 | Barr et al. | |
| 6,092,610 A | 7/2000 | Kosmala et al. | |
| 6,158,529 A | 12/2000 | Dorel | |
| 6,244,361 B1 | 6/2001 | Comeau et al. | |
| 6,364,034 B1 | 4/2002 | Schoeffler | |
| 6,394,193 B1 | 5/2002 | Askew | |
| 6,506,083 B1* | 1/2003 | Bickford | H01R 13/533 439/281 |
| 7,194,902 B1* | 3/2007 | Goodwin | E21B 49/10 73/152.24 |
| 7,222,671 B2 | 5/2007 | Caudwell et al. | |
| 2001/0052428 A1 | 12/2001 | Larronde et al. | |
| 2002/0011359 A1 | 1/2002 | Webb et al. | |
| 2006/0083941 A1* | 4/2006 | Lorenz | G01F 1/8404 428/544 |
| 2006/0137873 A1* | 6/2006 | Caudwell | G01N 11/16 166/252.5 |
| 2008/0159077 A1* | 7/2008 | Madhavan | E21B 17/028 367/76 |
| 2009/0120171 A1* | 5/2009 | Harrison | G01N 11/16 73/64.53 |
| 2010/0122817 A1* | 5/2010 | Surjaatmadja | E21B 34/14 166/308.1 |
| 2011/0023587 A1 | 2/2011 | Madhavan et al. | |
| 2011/0030455 A1* | 2/2011 | Matsumoto | G01N 11/16 73/54.41 |
| 2011/0083501 A1 | 4/2011 | Desroques et al. | |
| 2011/0252879 A1* | 10/2011 | Madhavan | E21B 47/065 73/152.33 |
| 2013/0186185 A1* | 7/2013 | Harrison | G01N 11/16 73/54.41 |
| 2015/0070000 A1* | 3/2015 | Gao | E21B 47/06 324/204 |

OTHER PUBLICATIONS

Caudwell et al, A robust vibrating wire viscometer for reservoir fluids: results for toluene and ndecane, 2004, Journal of Petroleum Science and Engineering vol. 44, Issues 3-4, Nov. 15, 2004, pp. 333-340.*

Mishra et al, Downhole Viscosity Measurement: Revealing Reservoir Fluid Complexities and Architecture, SPWLA 55,. Annual Logging Symposium, May 18-22, 2014.*

* cited by examiner

VIBRATING WIRE VISCOMETER AND CARTRIDGE FOR THE SAME

CROSS REFERENCE TO RELATED APPLICATIONS

This is a non provisional patent application of U.S. provisional patent application Ser. No. 62/057,238 to Cong Wang, et al filed on Sep. 30, 2014, which is hereby incorporated in its entirety for all intents and purposes by this reference.

BACKGROUND

This disclosure relates generally to viscometers for measuring viscosity of fluids and, more particularly, to vibrating wire viscometers that are suitable for applications relating to various types of downhole in oilfield or gasfield such as Measurement-While-Drilling (MWD), Logging-While-Drilling (LWD) and wireline logging applications.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of downhole petroleum and natural gas exploration, fluid property measurement under native or in situ conditions is an important tool to surveyors to understand the economic viability of a subterranean formation reservoir. Among the fluid properties of interest is viscosity. Viscosity measurements may be performed by exposing a wire to a downhole fluid to be measured and causing the wire to vibrate within the fluid. By measuring the loading effects of the fluid on the vibration of the wire, the viscosity of the downhole fluid may be determined.

As will become apparent from the following description and discussion, the present disclosure provides improved vibrating wire viscometers capable of easily enhancing measurement ranges of viscosity with high accuracy.

SUMMARY OF THE DISCLOSURE

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect of the present disclosures, a cartridge for a vibrating wire viscometer includes a body member with a flowline for passing fluid, an electrically conductive wire disposed in the flowline, first and second electrically conductive posts, and a connector having first and second electrically conductive terminals. The first and second posts are mechanically coupled to the body member to hold the wire in tension within the flowline. The first and second terminals are connected to the first and second posts for applying an alternating electric current to the wire, respectively.

In another aspect of the present disclosures, a vibrating wire viscometer housing includes a slot to hold a cartridge for a vibrating wire viscometer and a cavity to hold a magnet for generating a magnetic field in the slot. The cartridge includes a body member with a flowline for passing fluid, an electrically conductive wire disposed in the flowline, first and second electrically conductive posts, and a connector having first and second electrically conductive terminals. The first and second posts are mechanically coupled to the body member to hold the wire in tension within the flowline. The first and second terminals are connected to the first and second posts for applying an alternating electric current to the wire, respectively.

In yet another aspect of the present disclosures, a vibrating wire viscometer includes a cartridge, a magnet for generating a magnetic field in the flowline of the cartridge, a housing that includes a slot to hold the cartridge and a cavity to hold the magnet; and a circuit for applying the alternating electric current to the wire of the cartridge and measuring viscosity of the fluid passing through the flowline of the cartridge based on a resonant vibrating frequency of the wire. The cartridge includes a body member with a flowline for passing fluid, an electrically conductive wire disposed in the flowline, first and second electrically conductive posts, and a connector having first and second electrically conductive terminals. The first and second posts are mechanically coupled to the body member to hold the wire in tension within the flowline. The first and second terminals are connected to the first and second posts for applying an alternating electric current to the wire, respectively.

Advantages and novel features of the disclosures will be set forth in the description which follows or may be learned by those skilled in the art through reading the materials herein.

BRIEF DESCRIPTION OF THE DRAWINGS

Embodiments of vibrating wire viscometers and cartridges/housings for the same according to the disclosures herein are described with reference to the following figures. The same numbers are used throughout the figures to reference like features and components.

DETAILED DESCRIPTION

Illustrative embodiments and aspects of the present disclosure are described below. In the interest of clarity, not all features of an actual implementation are described in the specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such development effort might be complex and time-consuming, but would nevertheless be a routine undertaking for those of ordinary skill in the art having benefit of the disclosure herein.

Figure 1:
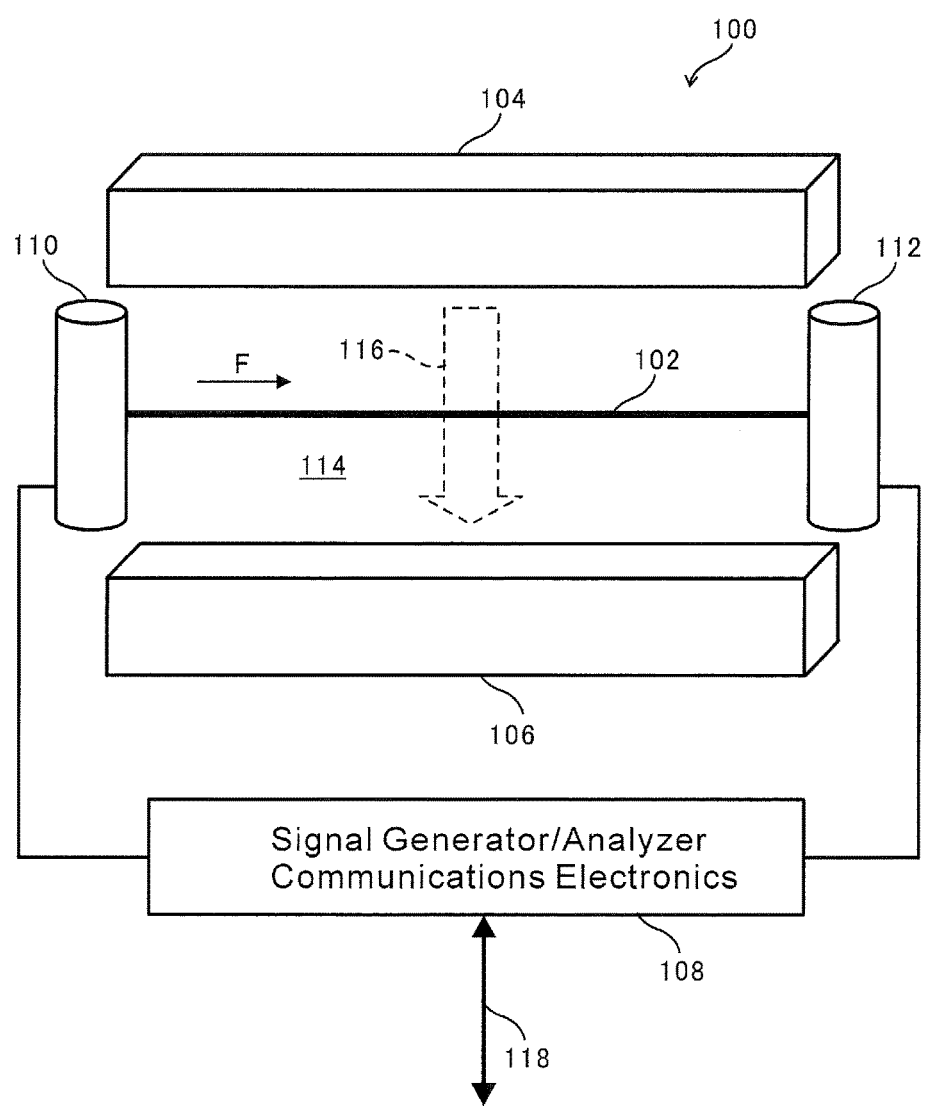
FIG. 1 is a schematic view of a vibrating wire viscometer according to one embodiment of the disclosures herein.

Referring now to FIG. 1, a vibrating wire viscometer 100 according to one embodiment of the disclosures herein is used for measurements of viscosity of fluids and includes a wire 102, magnets 104 and 106, and electronics 108. The wire 102 is made of electrically conductive material such as metal, normal alloy and superalloy (for example nickel-based superalloy). Both ends of the wire 102 are supported by electrically conductive posts 110 and 112 so that the wire 102 is tensioned with a certain tension and disposed within a flowline 114 in which a magnetic field 116 is generated across the wire 102 by the magnets 104 and 106. The posts 110 and 112 are made of electrically conductive material and coupled to the electronics 108.

The electronics 108 includes circuits for applying an alternating electric current to the wire 102 and measuring viscosity of the fluid passing through the flowline 114 in the direction indicated by arrow F in FIG. 1, based on a resonant vibrating frequency of the wire 102 in the magnetic field 116. The electronics 108 may be configured to cause the wire 102 to vibrate as a signal generator, to measure the viscosity of the fluid via the wire 102 as an analyzer, and/or to communicate with additional tools along a drillstring or wireline tool via a cable 118 as communications, as described in U.S. Patent Application Publication Nos. 2011/0023587 and 2011/0083501 which are incorporated herein by reference in its entirety.

To measure the viscosity of a fluid within the flowline 114, the electronics 108 generate a sinusoidal or other signal at a predetermined frequency. The signal travels from the electronics 108 to the post 110. The post 110 is electrically coupled to the wire 102, which conducts the signal to the wire 102 and to the other post 112. The post 112 is electrically coupled to the electronics 108. Thus, the electronics 108 may apply an alternating current to the wire 102. At a particular frequency, based on mechanical properties such as material, length Lw, diameter and tension of the wire 102, the wire 102 vibrates with a displacement of about 20 [μm] at a resonant frequency within the magnetic field 116 provided by the magnets 104 and 106.

Based on the viscosity of the fluid surrounding the wire 102, the vibration of the wire 102 may be damped and decay mostly of friction drag force of the viscous surrounding fluid to the wire 102, and/or additional power may be required to continue to vibrate the wire 102 at the resonant frequency. The closer the magnets 104, 106 are to the vibrating wire 102, the stronger the magnetic field 116 will be and the stronger the amplitude of the vibration of the wire 102. A reverse voltage is generated as a result of the vibrating wire 102 and the magnetic field as a back electromotive force (emf). The reverse voltage may be measured by the electronics 108 to determine the viscosity of the fluid. A further explanation of the use of a vibrating wire method to determine the viscosity of a fluid may be found in U.S. Pat. No. 7,222,671 which is incorporated herein by reference in its entirety.

As discussed above, the measured viscosity of fluid may be determined based on the reverse voltage (emf) at a certain resonant frequency of the wire 102 and the resonant frequency may be generated based on mechanical properties such as material, length Lw, diameter and tension of the wire 102. Thus, a measurable range of viscosity with high accuracy by using the vibrating wire viscometer 100 may be determined and restricted by the mechanical properties of the wire 102. Furthermore, the measurement range of viscosity is difficult to control to be within a certain range and change to other range because of uncertain tension of the wire 102 after anchoring to the posts 110 and 112 by welding process such as a laser welding. Under the background, the vibrating wire viscometer 100 according to embodiments of the disclosures herein has a structure using a cartridge attaching/detaching for a housing of the vibrating wire viscometer 100, which is capable of easily enhancing measurement ranges of viscosity with high accuracy.

Figure 2:
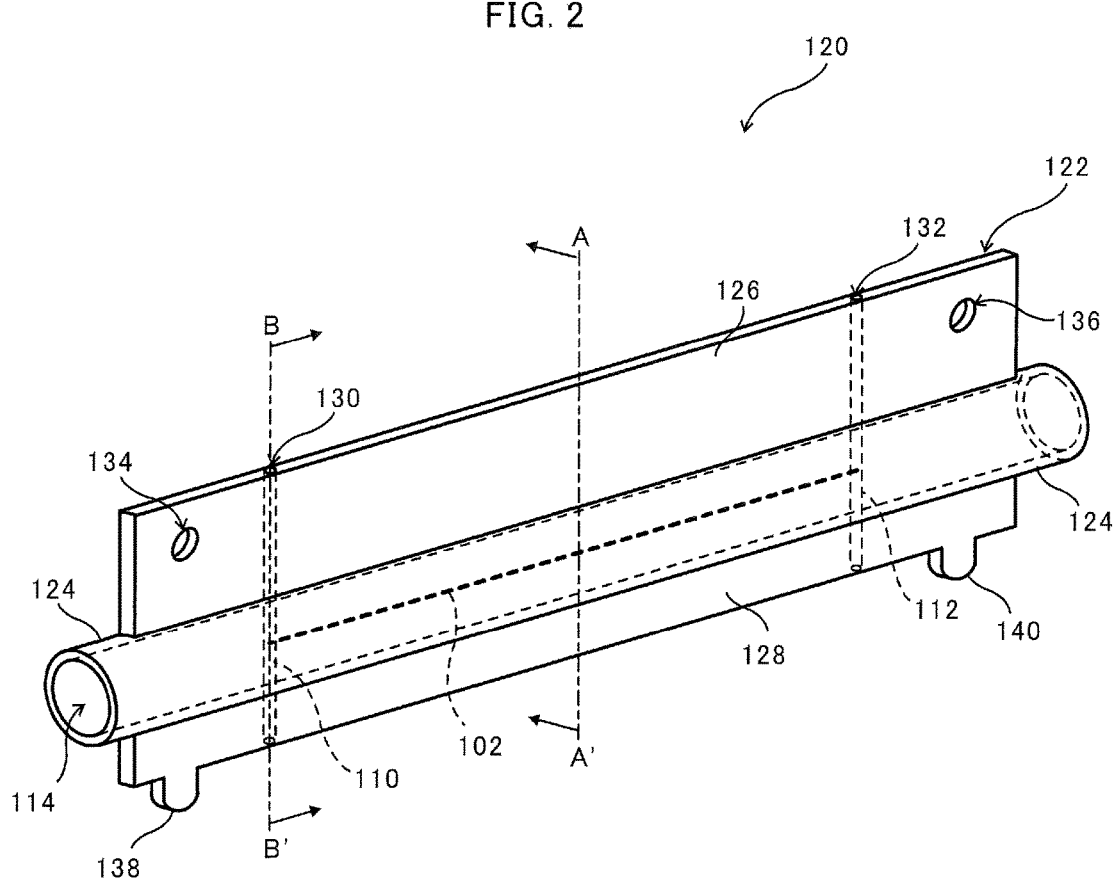
FIG. 2 is a perspective view of a cartridge of a vibrating wire viscometer of the disclosures herein.

FIG. 2 is a perspective view of a cartridge for a vibrating wire viscometer of the disclosures herein. The cartridge 120 includes a body member 122 with a flowline 114 for passing fluid, an electrically conductive wire 102 disposed in the flowline 114, first and second electrically conductive posts 110 and 112, and a connector having first and second electrically conductive terminals or receptacles described elsewhere herein. The posts 110 and 112 are made of electrically conductive material such as metal and mechanically coupled to the body member 122 to hold and dispose the wire 102 in tension via a sealing material within the flowline 114.

The body member 122 has a tubular part 124 forming the flowline 114 inside and at least one planer guide parts that extends radially outward from an outer peripheral surface of the tubular part 124. In the embodiment of FIG. 2, the at least one planer guide parts are configured with a upper planer guide part 126 and a lower planer guide part 128. The planer guide part 126 and 128 are guided by slits of a housing when the cartridge 120 is inserted in the housing as described elsewhere herein. The body member 122 further includes two through-holes 130 and 132 so as to pass through within the upper planer guide part 126 and the lower planer guide part 128 crossing a center axis of the flowline 114. The respective posts 110 and 112 are inserted in the through-holes 130 and 132 and fixed to cross a center axis of the flowline 114. The upper planer guide part 126 has two through-holes 134 and 136 for inserting secure spiral pins to fix the cartridge 120 within a housing. The lower planer guide part 128 has two protruding part 138 and 140 for preventing rotation the body member 120.

Figure 3A:
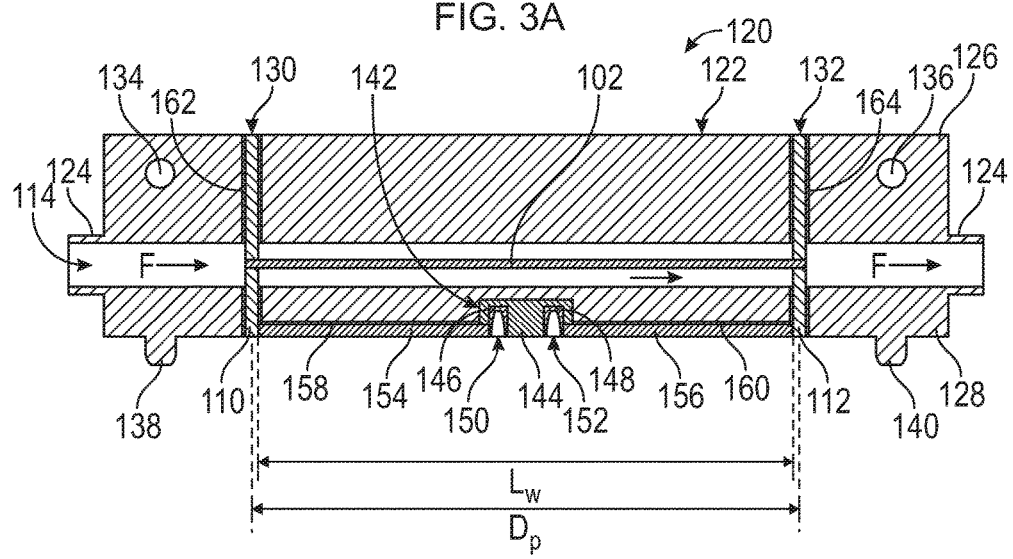
FIG. 3A is a cross-sectional view of the cartridge 120, taking along line A-A' in FIG. 2
Figure 3B:
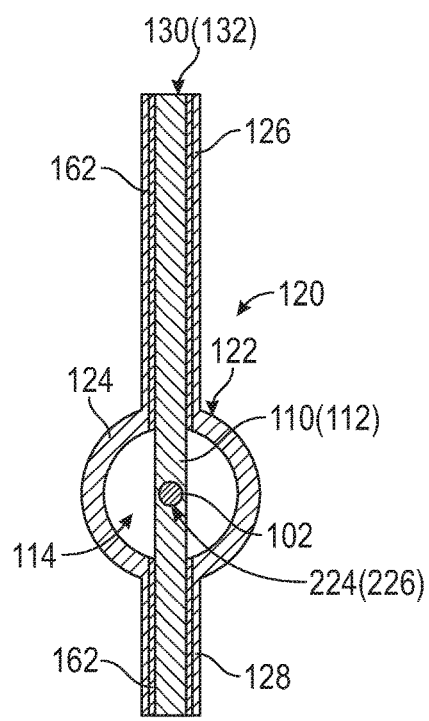
FIG. 3B is a cross-sectional view of the cartridge 120, taking along line B-B' in FIG. 2.

FIG. 3A is a cross-sectional view of the cartridge 120, taking along line A-A' in FIG. 2 and FIG. 3B is a cross-sectional view of the cartridge 120, taking along line B-B' in FIG. 2. The body member 122 including the tubular part 124 and the planer guide part 126, 128 is made of electrically conductive material such as metal. The posts 110 and 112 are disposed with a predetermined post distance Dp by inserting into the through-holes 130 and 132. The posts 110 and 112 within the through-holes 130 and 132 are electrically insulated from the body member 122 via a sealing material such as glass or ceramic seal 162. The seal 162 is filled within the space between outer surfaces of the posts 110 and 112 and inner surfaces of the through-holes 130 and 132, and has a function to rigidly support the posts 110 and 112 as well as the electrical insulating.

A connector 142 may be formed within central portion of lower side of the lower planer guide part 128. The connector 142 includes an electrically insulated body part 144 and two electrically conductive receptacles 146 and 148 formed in the body part 144. The respective receptacles 146 and 148 are electrically conductive and have pin slots 150 and 152 that are functioned as pin insertion holes to be inserted with connecting pins from the housing. The receptacles 146 and 148 are connected to the posts 110 and 112 via lead wires 158 and 156 for applying an alternating electric current to the wire 102, respectively. The lead wires 158 and 160 are electrically insulated from the lower planer guide part 128 of the body member 122 via insulating layer 154 and 156.

The posts 110 and 112 may be disposed just crossing a center axis of the flowline 114 and have open holes 224 and 226 to be located at the center axis as shown in FIG. 3B. Both ends of the wire 102 are held and fixed in the open hole 224 and 226 by welding such as a laser welding so that the wire 102 rigidly supported with the posts 110 and 112.

In this embodiment, two or more types of cartridges 120 with different range of viscosity measurements each other may prepared by changing at least one of mechanical properties such as material, length Lw, diameter and tension of the wire 102. Among the plural types of cartridges, one appropriate cartridge with target range of viscosity measurements can be selected and attached to a housing so as to configure a completed vibrating wire viscometer 100.

Figure 4:
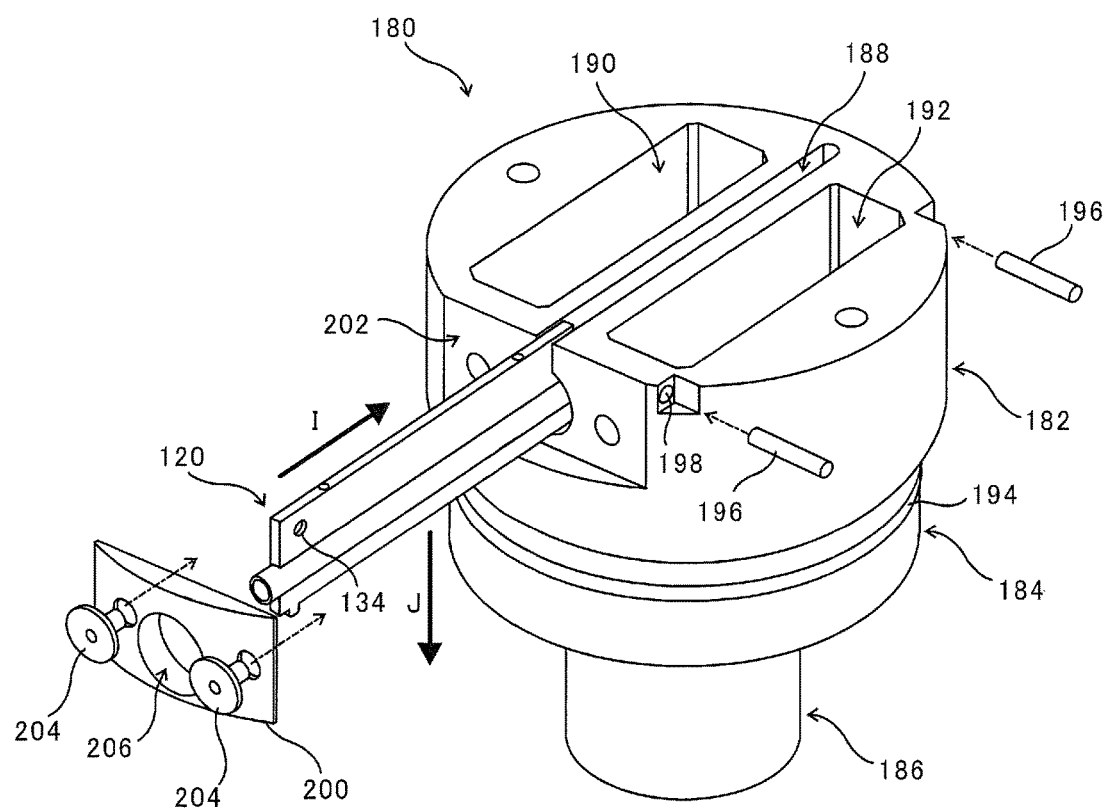
FIG. 4 is a perspective view of a housing of a vibrating wire viscometer of the disclosures herein.

FIG. 4 is a perspective view of a housing of a vibrating wire viscometer of the disclosures herein. The housing 180 includes a sensor head part 182, a base part 184 and a receptacle connector 186. The sensor head part 182 has a slot 188 to hold a cartridge 120 for a vibrating wire viscometer 100 and two cavities 190 and 192 to hold magnets for generating a magnetic field in the slot 188. Upper and lower slit spaces of slot 188 may be formed to approximately fit outer shape of the upper planer guide part 126 and lower planer guide part 128 of cartridge 120 and a central cylindrical space may be formed to have a larger internal diameter than the outer diameter of the tubular part 124 of the cartridge 120. Two recessed (or concave) parts (referred to as 230 in FIG. 5A in part) to be engaged with the two protruding part 138 and 140 of the cartridge 120 are formed at bottom surface of the lower slit. The respective cavities 190 and 192 may be formed so as to hold the magnets by molding. An O-ring 194 may be arranged to a groove on an outer spherical circumference surface of the base part 184 to prevent a leakage of fluid from upper side space having the sensor head part 182 to lower side space having the receptacle connector 186.

The cartridge 120 can be mounted in the housing 180 by inserting into the slot 188 in the direction indicated by arrow I and then shifting downward in the direction indicated by arrow J in FIG. 4. After mounting into the slot 188, the cartridge 120 is fixed by setting secure spiral pins 196 into the through-holes 134 and 136 of the cartridge 120 via through-holes 198 of the sensor head part 182. A front side of the cartridge 120 is held by attaching a cap member 200 on a side-receiving surface 202 of the sensor head part 182 by using lock pins 204. An opening of the tubular part 124 as an inlet of the fluid is exposed on an opening 206 formed at a center of the cap member 200. A top surface of the sensor head part 182 may be also covered with a cap member.

Figure 5A:
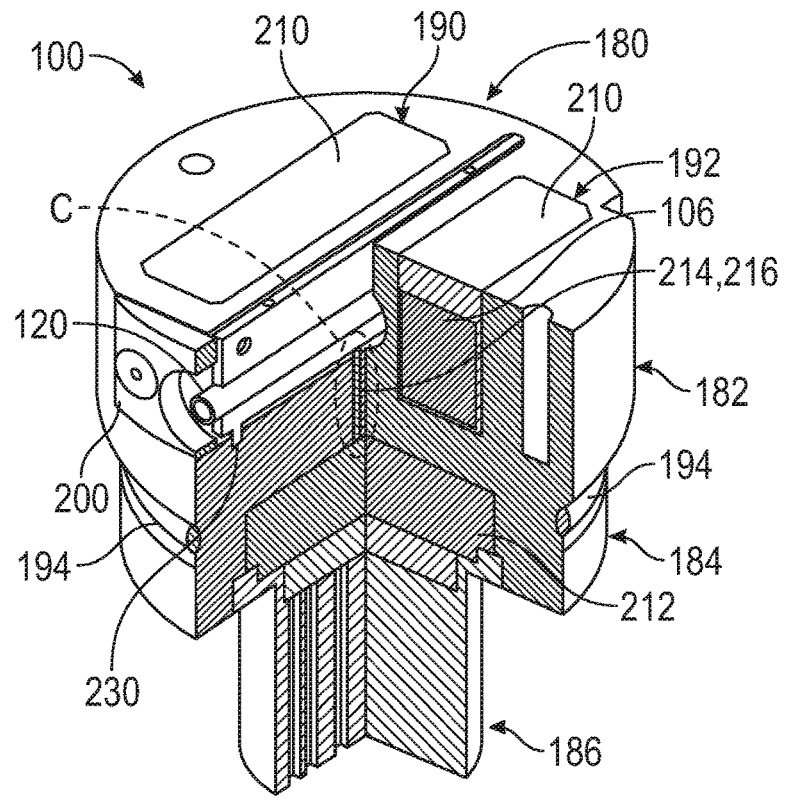
FIG. 5A is a partially-sectional perspective view of a vibrating wire viscometer after mounting a cartridge of the disclosures herein and FIG. 5B is an enlarged view around a electrical connection in area C indicated in FIG. 5A.
Figure 5B:
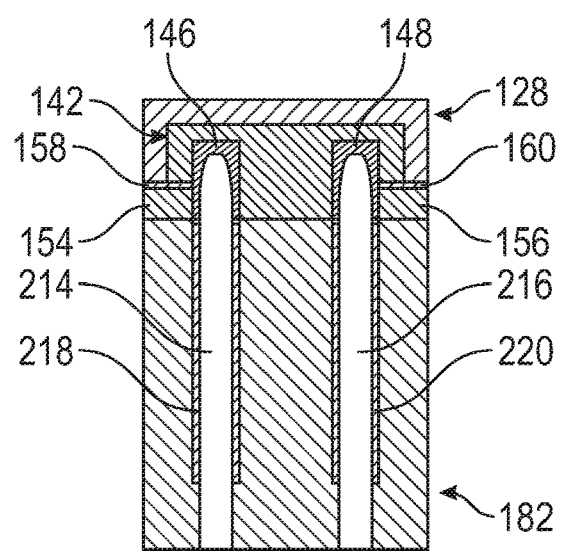

FIG. 5A is a partially-sectional perspective view of a vibrating wire viscometer after mounting a cartridge of the disclosures herein and FIG. 5B is an enlarged view around an electrical connection in area C indicated in FIG. 5A. Magnets 106 (104) are disposed in the cavities 190 and 192 and held by molding 210 with synthetic resin material such as PEEK (polyetheretherketone), so that the cartridge 120 is located at almost center of a distance between the magnets 106 (104). A PWA (printed-wiring assembly-) 212 embedded in the base part 184 of housing 180 includes a circuit for applying the alternating electric current to the wire 102 of the cartridge 120 and measuring viscosity of the fluid passing through the flowline 114 of the cartridge based on a resonant vibrating frequency of the wire 102. The PWA 212 may correspond to the foregoing electronics 108 having functions of signal generator, analyzer and communications. The PWA 212 is electrically connected with the receptacles 146 and 148 of connector 142 via feedthrough posts 214 and 216 embedded in through-holes formed in the base part 184 of housing 180. Annular gaps between the through-holes of the base part 184 and the feedthrough posts 214, 216 may be sealed by pressure seal 218 and 220 such as glass seal as shown in FIG. 5B so as to prevent a leakage of pressure from upper side space of the slot 188 having the cartridge 120 to lower side space having the receptacle connector 186.

Figure 6:
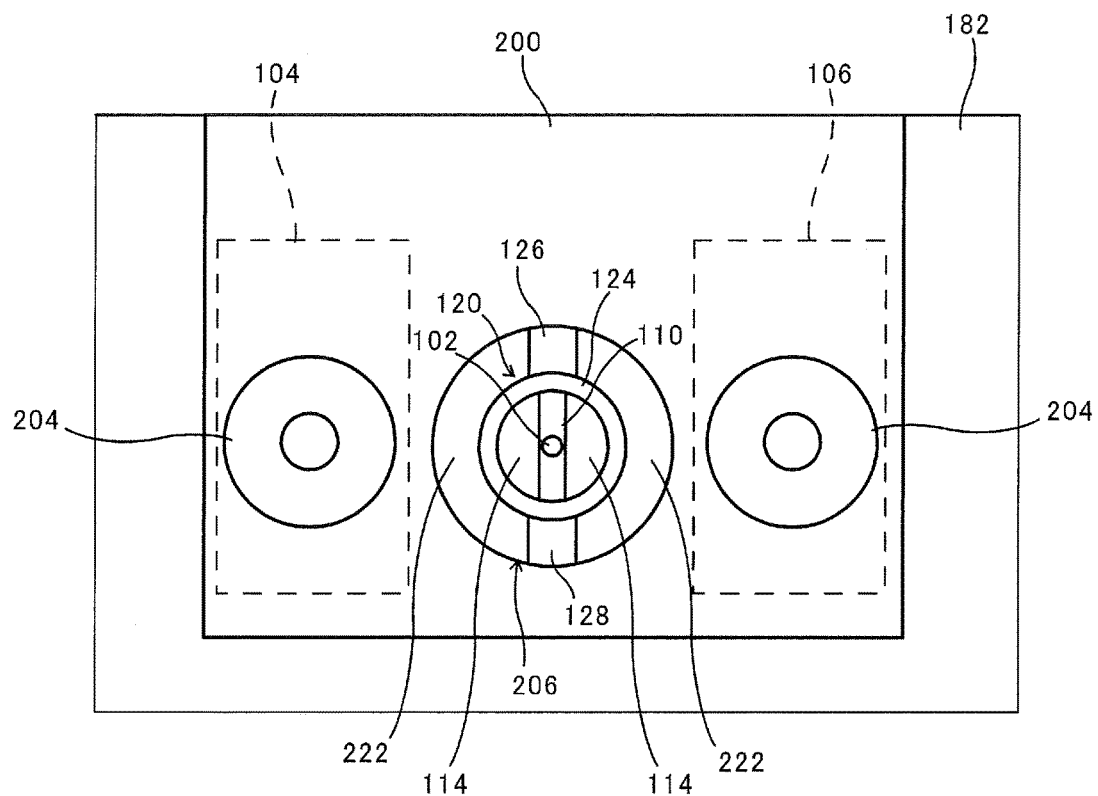
FIG. 6 is a partial side view of a vibrating wire viscometer of the disclosures herein.

FIG. 6 is a partial side view of a vibrating wire viscometer of the disclosures herein. Both end openings of the tubular part 124 of the cartridge is exposed to outside as an inlet of the fluid via the opening 206 of the cap member 200. An internal diameter of the opening 206 is larger than the outer diameter of the tubular part 124 of the cartridge 120. Furthermore, as described elsewhere herein, the central cylindrical space of the slot 188 in the housing 180 is formed to have a larger internal diameter than the outer diameter of the tubular part 124 of the cartridge 120. This structure may lead to forming concentrically dual flowlines which are the internal flowline 114 for measurements of viscosity and a bypass flowline 222 of the fluid. The structure of concentrically dual flowlines has an advantage to reduce effect due to magnetic particles in the fluid. As the flowline 114 for viscosity measurements is positioned in the magnetic field 116 (see FIG. 1), magnetic particles in the fluid may get trapped in the flowline 114. In the vibrating wire viscometer 100 of the disclosures herein, the magnetic particles will mainly be accumulated in the outer bypass flowline 222 instead of in the internal flowline 114 so as to reduce the effect due to magnetic particles in the flowline 114 for viscosity measurements. Moreover, the structure of concentrically dual flowlines has another advantage to reduce damage to the posts 110 and 112. The sampling fluid in the flowline 114 may tend to be laminar flow having little turbulent with small particles so that the damage due to erosion from the turbulent with small particles can be reduced.

According to the embodiments of the vibrating wire viscometer 100 disclosed herein, the cartridge 120 can be easily replaced by loosening the lock pins 204 of the cap member 200 and sliding the cartridge 120 off from the housing 180. By designing different types of cartridges 100 with different mechanical properties such as material, length, diameter and tension of the wire 102, the resonance frequency of the wire 102 can be changed and range and accuracy in certain range for viscosity measurements can be improve while the housing 180 including the PWA 212 is not replaced and used for the different types of cartridges. This enable a serials of different configuration design to suit different reservoirs with varies downhole fluid viscosity. Furthermore, as the cartridge 120 can be disassembled from the housing 180, it is easier to do maintenance by disassembling the sensing element such as the wire 102 out from the cartridge 120 and/or toe housing 180. Moreover, the vibrating wire viscometer 100 is fully repairable by changing the cartridge 120 when there is an issue such as broken wire.

Figure 7:
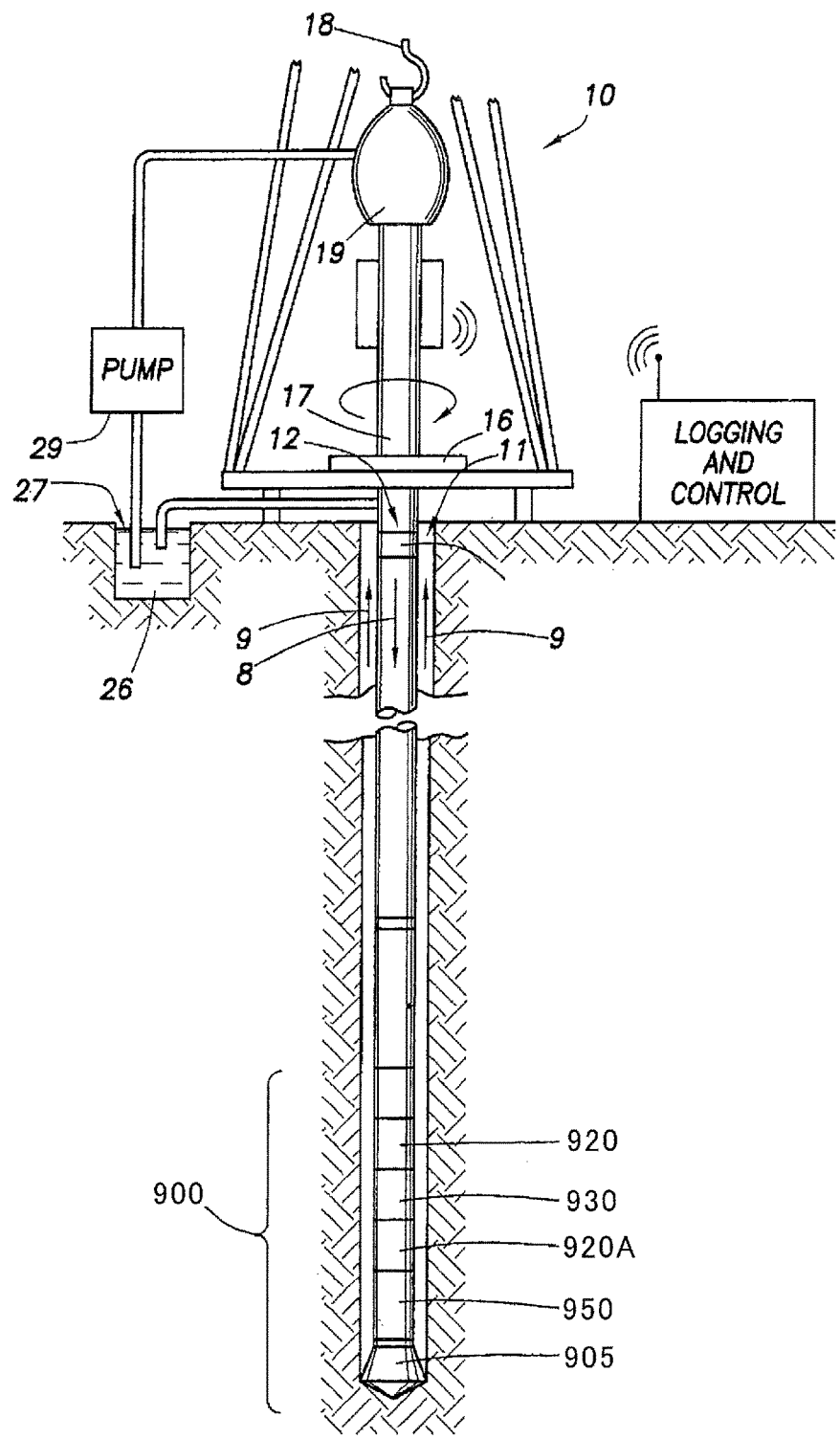
FIG. 7 is a schematic diagram of an apparatus including the vibrating wire viscometer of the disclosures herein, which is used in a well passing through earth formations.

FIG. 7 illustrates a wellsite system in which at least one of the vibrating wire viscometers of the disclosures herein can be employed. The wellsite can be onshore or offshore. In this system, a borehole 11 is formed in subsurface formations by rotary drilling in a manner that is well known.

Embodiments of the disclosures can also use directional drilling, as will be described hereinafter.

A drill string 12 is suspended within the borehole 11 and has a bottom hole assembly 900 which includes a drill bit 105 at its lower end. The surface system includes platform and derrick assembly 10 positioned over the borehole 11, the assembly 10 including a rotary table 16, kelly 17, hook 18 and rotary swivel 19. The drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is well known, a top drive system could alternatively be used.

In the example of this embodiment, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 905, and then circulates upwardly through the annulus region between the outside of the drill string and the wall of the borehole, as indicated by the directional arrows 9. In this well known manner, the drilling fluid lubricates the drill bit 905 and carries formation cuttings up to the surface as it is returned to the pit 27 for recirculation. The bottom hole assembly 900 of the illustrated embodiment a logging-while-drilling (LWD) module 920, a measuring-while-drilling (MWD) module 930, a roto-steerable system and motor, and drill bit 905.

The LWD module 920 is housed in a special type of drill collar, as is known in the art, and can contain one or a plurality of known types of logging tools. It will also be understood that more than one LWD and/or MWD module can be employed, e.g. as represented at 920A. (References, throughout, to a module at the position of 920 can alternatively mean a module at the position of 920A as well.) The LWD module includes capabilities for measuring, processing, and storing information, as well as for communicating with the surface equipment. In the present embodiment, the LWD module includes at least one of the vibrating wire viscometers.

The MWD module 930 is also housed in a special type of drill collar, as is known in the art, and can contain one or more devices such as the vibrating wire viscometer for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a viscosity measuring device, a weight-on-bit measuring device, a torque measuring device, a vibration measuring device, a shock measuring device, a stick slip measuring device, a direction measuring device, and an inclination measuring device.

A particularly advantageous use of the system hereof is in conjunction with controlled steering or "directional drilling." In this embodiment, a roto-steerable subsystem 950 is provided. Directional drilling is the intentional deviation of the wellbore from the path it would naturally take. In other words, directional drilling is the steering of the drill string so that it travels in a desired direction. Directional drilling is, for example, advantageous in offshore drilling because it enables many wells to be drilled from a single platform. Directional drilling also enables horizontal drilling through a reservoir. Horizontal drilling enables a longer length of the wellbore to traverse the reservoir, which increases the production rate from the well. A directional drilling system may also be used in vertical drilling operation as well. Often the drill bit will veer off of a planned drilling trajectory because of the unpredictable nature of the formations being penetrated or the varying forces that the drill bit experiences. When such a deviation occurs, a directional drilling system may be used to put the drill bit back on course. A known method of directional drilling includes the use of a rotary steerable system ("RSS"). In an RSS, the drill string is rotated from the surface, and downhole devices cause the drill bit to drill in the desired direction. Rotating the drill string greatly reduces the occurrences of the drill string getting hung up or stuck during drilling. Rotary steerable drilling systems for drilling deviated boreholes into the earth may be generally classified as either "point-the-bit" systems or "push-the-bit" systems. In the point-the-bit system, the axis of rotation of the drill bit is deviated from the local axis of the bottom hole assembly in the general direction of the new hole. The hole is propagated in accordance with the customary three-point geometry defined by upper and lower stabilizer touch points and the drill bit. The angle of deviation of the drill bit axis coupled with a finite distance between the drill bit and lower stabilizer results in the non-collinear condition required for a curve to be generated. There are many ways in which this may be achieved including a fixed bend at a point in the bottom hole assembly close to the lower stabilizer or a flexure of the drill bit drive shaft distributed between the upper and lower stabilizer. In its idealized form, the drill bit is not required to cut sideways because the bit axis is continually rotated in the direction of the curved hole. Examples of point-the-bit type rotary steerable systems, and how they operate are described in U.S. Patent Application Publication Nos. 2002/0011359; 2001/0052428 and U.S. Pat. Nos. 6,394,193; 6,364,034; 6,244,361; 6,158,529; 6,092,610; and 5,113,953 all herein incorporated by reference. In the push-the-bit rotary steerable system there is usually no specially identified mechanism to deviate the bit axis from the local bottom hole assembly axis; instead, the requisite non-collinear condition is achieved by causing either or both of the upper or lower stabilizers to apply an eccentric force or displacement in a direction that is preferentially orientated with respect to the direction of hole propagation. Again, there are many ways in which this may be achieved, including non-rotating (with respect to the hole) eccentric stabilizers (displacement based approaches) and eccentric actuators that apply force to the drill bit in the desired steering direction. Again, steering is achieved by creating non co-linearity between the drill bit and at least two other touch points. In its idealized form the drill bit is required to cut side ways in order to generate a curved hole. Examples of push-the-bit type rotary steerable systems, and how they operate are described in U.S. Pat. Nos. 5,265,682; 5,553,678; 5,803,185; 6,089,332; 5,695,015; 5,685,379; 5,706,905; 5,553,679; 5,673,763; 5,520,255; 5,603,385; 5,582,259; 5,778,992; 5,971,085 all herein incorporated by reference.

The preceding description has been presented only to illustrate and describe certain embodiments. It is not intended to be exhaustive or to limit the disclosures to any precise form disclosed. Many modifications and variations are possible in light of the above teaching.

The embodiments and aspects were chosen and described in order to best explain principles of the disclosures and its practical applications. The preceding description is intended to enable others skilled in the art to best utilize the principles in various embodiments and aspects and with various modifications as are suited to the particular use contemplated. It is intended that the scope of the disclosures be defined by the following claims.

What is claimed is:

1. A viscosity measurement assembly comprising:
   a housing that comprises slits;
   a tubular flowline disposed between an upper planar guide part and a lower planar guide part; and
   an electrically conductive wire disposed in the tubular flowline between posts that are supported by the guide parts,
   wherein the guide parts are received by the slits of the housing to define a bypass flowline with respect to the housing that is concentric to the tubular flowline,
   wherein the bypass flowline comprises a cross-sectional flow area that is greater than a cross-sectional flow area of the tubular flowline,
   wherein the housing comprises magnets proximate to the bypass flowline,
   wherein the bypass flowline, via said bypass flowline's proximity to the magnets and greater cross-sectional flow area, diverts magnetic particles concentrically away from the tubular flowline, and
   wherein the diversion of magnetic particles to the bypass flowline enhances laminar flow in the tubular flowline along the electrically conductive wire.

2. The viscosity measurement assembly of claim 1 wherein the tubular flowline comprises first and second through-holes, wherein the posts comprise first and second posts, and wherein the first and second posts are inserted in the first and second through-holes to cross a center axis of the tubular flowline.

3. The viscosity measurement assembly of claim 2 wherein the first and second posts are electrically insulated from the tubular flowline via a glass or ceramic seal.

4. The viscosity measurement assembly of claim 2, wherein the first and second posts include a through-hole in which the electrically conductive wire is inserted and fixed to hold the electrically conductive wire along a center axis of the tubular flowline, respectively.

5. The viscosity measurement assembly of claim 1, further comprising a connector for applying alternating electric current to the electrically conductive wire via the posts.

6. The viscosity measurement assembly of claim 1, configured for measurements of viscosity of a fluid in a downhole of an oilfield or a gasfield.

\* \* \* \* \*